United States Patent [19]

Hope

[11] Plant 4,306

[45] Sep. 26, 1978

[54] KALANCHOE PLANT

[75] Inventor: Claude Hope, Cartago, Costa Rica

[73] Assignee: Mikkelsens, Inc., Ashtabula, Ohio

[21] Appl. No.: 823,851

[22] Filed: Aug. 11, 1977

[51] Int. Cl.[2] ..... A01H 5/00

[52] U.S. Cl. ..... Plt./68

[58] Field of Search ..... Plt./68

*Primary Examiner*—Robert E. Bagwill

*Attorney, Agent, or Firm*—Beall & Jeffery

[57] ABSTRACT

A new asexually reproduced kalanchoe characterized by its intense bright red purple flower color, uniform mounded inflorescence, and broad versatility of sizes of plants that can be produced with equal keeping qualities regardless of size.

1 Drawing Figure

The present invention relates to a new and distinctive variety of kalanchoe plant, known by the cultivar name Adagio and botanically known as Kalanchoe, developed by me through controlled breeding by crossing selected Swiss Rose clone #2 (seed parent) with commercial seed strain Swiss Rose (pollen parent). Both parents are unpatented. Asexual reproduction of stem cuttings has shown that the unique features of this new kalanchoe are stabilized and are reproduced true to type in successive propagations.

The following characteristics distinguish the new kalanchoe from both its parent varieties and other cultivated kalanchoes of this type known and used in the floriculture industry:

1. In comparison to the seed produced strain, the color of my new selection is more intense and the flowers have much better keeping qualities. The new cultivar does not come true to type for commercial seed production.

2. In comparison to my seedling M-12, known by the cultivar name Largo and disclosed in an application filed simultaneously herewith, the plant growth and general habits are quite similar but the flower color of Largo is considerably lighter and has a greater tendency to fade. Flower petals of Adagio are wider and shorter than Largo.

3. The intense, bright red purple color of the flower petals.

4. The extremely long keeping qualities of the flowers, which have been known to remain in excellent condition in the home for 10 to 12 weeks. As illustrated, flowering is quite uniform.

5. The large quantity of blooms in flower at one time, thereby presenting a floral display twice the diameter of the extremities of the foliage. Mildew has not been observed to date on my new cultivar.

6. Quite small compact foliage for kalanchoes, allowing for pot to pot growing up to the time of flower development. This is of economic importance to the flowering pot plant producer.

7. Profuse self-branching habit which is of economic importance to the propagator and to the finished plant producer. My new cultivar is ideally suited for small pot plant production.

8. The excellent and rapid rooting qualities of top stem cuttings, with the rooting being less than 21 days when the propagation media is 21°-22° C.

9. Research has determined that my new cultivar is ideally suited for production of miniature flowering kalanchoe plants as illustrated in FIG. 2 of the photographic drawings. Unrooted cuttings of the plant shown therein were stuck directly into 5 cm. pots and placed directly into short day treatment on 5.5 cm. centers. Such flowering plants can be used in terrariums or combination flowering pots. Most kalanchoes become too tall or "stretched" when given this technique of producing miniature flowering plants.

10. Additional flowering trails indicate that my new cultivar also can be produced in 15 cm. pots by allowing additional time for plant development before pinching and giving short day treatment. Thus my new cultivar has very broad versatility for production purposes.

The accompanying colored photographs illustrate the overall appearance of this variety taken as face views of the plants and showing the colors as true as it is reasonably possible to obtain in colored reproductions of this type.

FIG. 1 comprises a large plant grown under lights in a peat/perlite media in a 12 cm. clay pot, having been potted Dec. 20, 1976, pinched and given short day treatment Feb. 7, 1977, and flowered May 2, 1977. This plant was approximately 20 cm. in height and 25 cm. in diameter. The photograph comprising FIG. 1 was taken May 24, 1977.

FIG. 2, as above noted, comprises plants the cuttings of which were placed in a 5 cm. pot, with the result being a miniaturization of the plants and reduced flower size.

The following is a detailed description of my new kalanchoe variety based on plants produced under commercial practices in Costa Rica and Ashtabula, Ohio. Color references are made to the Royal Horticultural Society Colour Chart except where general terms of ordinary dictionary significance are used.

Parentage: Selected clone #2 of Swiss Rose crossed with commercial seed strain of Swiss Rose, and specifically selected out of the fifth seedling generation.

Propagation:

(A) *Type cutting.*—Vegetative terminal stem cuttings in 5 cm. pots.

(B) *Time to root.*—15-18 days at 22° C summer, 20-25 days at 21° C winter.

(C) *Rooting habit.*—Very rapid, profuse, dendritic, fibrous.

Plant description:

(A) *Form.*—Short, bushy, compact, vigorously upright.

(B) *Habit of growth.*—Slow, self-branching.

(C) *Foliage description.*—Small, dark green, close internode, slightly concave upward, nearly horizontal to approximately 15° above horizontal except where side shoots may force leaf to greater angle. (1) Size: From 3 cm. wide by 6 cm. long, petiole 15 mm. long, base nearly acute, apex toward acute. (2) Shape: From oval to elliptical. (3) Texture: Glabrous, coriaceous. (4) Margin: Crenate. (5) Color: Mature foliage top side darker green than 136A, underside near 139B.

Flowering description:

(A) *Flowering habits.*—Inflorescence develops very uniformly on nearly every peduncle, thereby giving a massive display of flowers best described as a paniculate cyme. The subcymes usually carry 15 to 20 flowers.

(B) *Natural flowering season.*—Under good light conditions is late December, and under adverse light conditions is early to mid-January. Flowering time under controlled daylength at 22° C in summer is 68–70 days, in winter is 85–87 days. Flowering time varies considerably with the intensity and duration of day light.

(C) *Flower buds.*—Typical for kalanchoes, being tubular, with the petals being wrapped. The bud measures approximately 2 mm. in diameter by 7 mm. long, and up to 13 mm. long when opened.

(D) *Flowers borne.*—Small flowering groups in cymes carried collectively on stiff wiry peduncles making up a paniculate cyme.

(E) *Quantity of flowers.*—Flowering shoots originate in nearly every leaf axil, flowering developing from apex to the crown, profuse and uniform.

(F) *Petals.*—(1) Shape: Elliptical. (2) Color: Top side when opening red purple 74B with very little fading throughout development, from 74B toward 74C; under side red purple 74C-D. (3) Number of petals: Four, 4 mm. wide by 6–7 mm. long; flower diameter 14 mm.

(G) *Reproductive organs.*—(1) Stamens: Eight in number. (a) Anther: anvil flat shape, color light brown. (b) Filament color: Translucent green. (c) Pollen color: Light yellow. (2) Pistils: (a) Stigma: shape coalesced, irregular, color pinkish white. (b) Style: Light green in color. (c) Ovaries: Four in number, size 5 mm., color green; produces good viable but variable seed.

Disease resistance: No diseases observed to date other than common botrytis.

I claim:

1. A new and distinct cultivar of kalanchoe known by the cultivar name Adagio and characterized particularly as to uniqueness by the combined characteristics of intense red purple flower color; excellent keeping qualities of the flowers; large floral display; small compact foliage; profuse self-branching; rapid rooting habit, and by the characteristic of being ideally suited for either normal or miniature flowering.

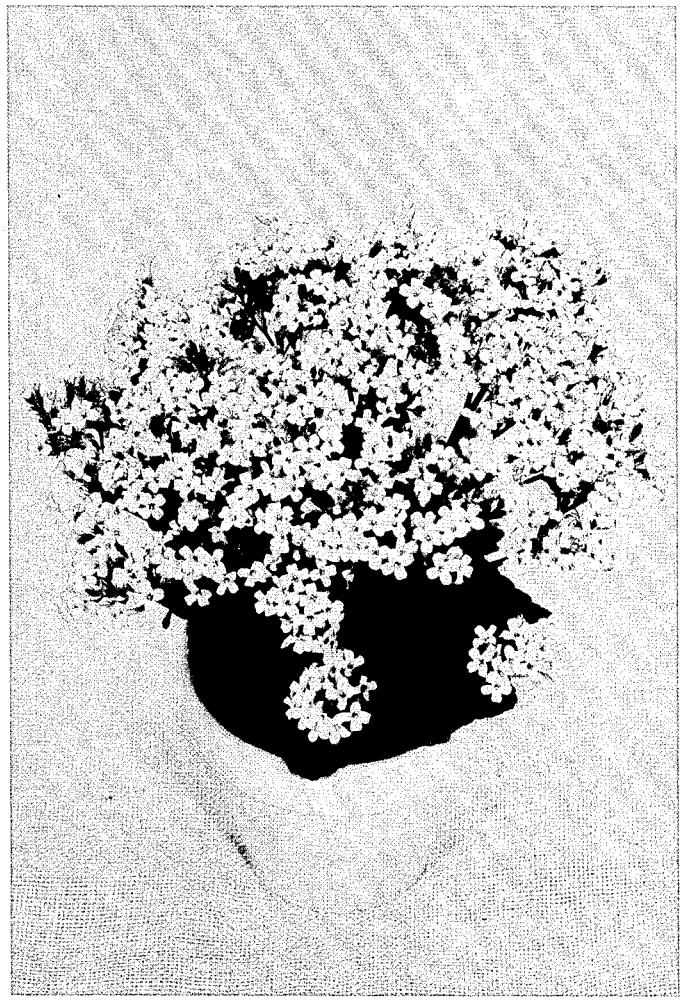

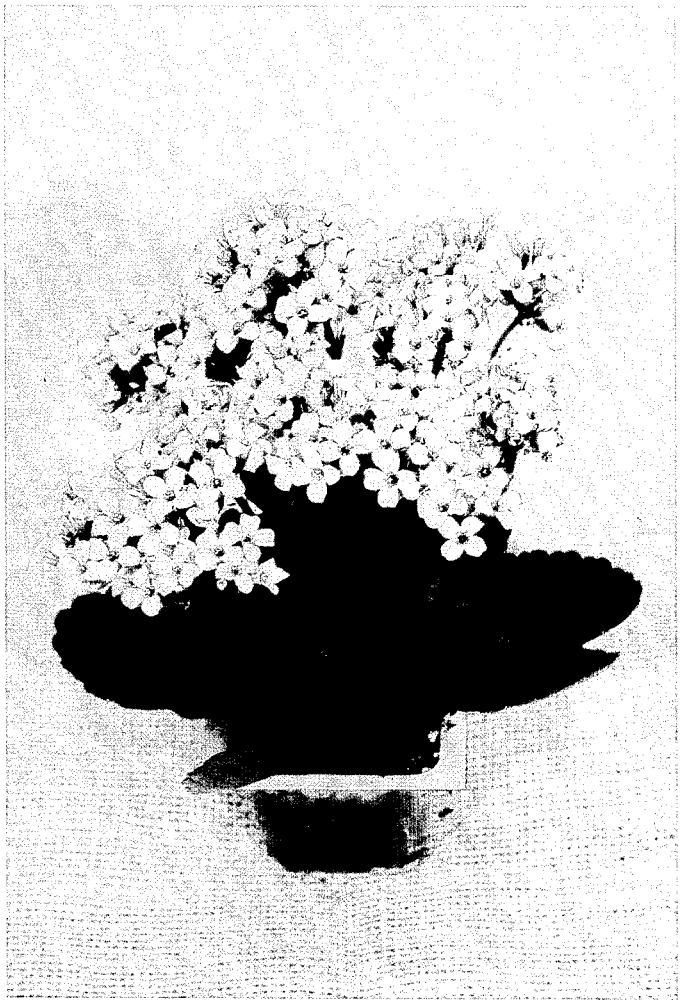

* * * * *